US008563024B2

(12) United States Patent
Bratt et al.

(10) Patent No.: US 8,563,024 B2
(45) Date of Patent: Oct. 22, 2013

(54) BIODEGRADABLE MATERIAL COMPONENTS

(75) Inventors: John Stephen Bratt, Newcastle (GB);
John Joseph Cooper, Crewe (GB);
Russell David Waters, Knutsford (GB)

(73) Assignee: Biocomposites Ltd., Staffordshire (GB)

( * ) Notice: Subject to any disclaimer, the term of this patent is extended or adjusted under 35 U.S.C. 154(b) by 317 days.

(21) Appl. No.: 12/726,759

(22) Filed: Mar. 18, 2010

(65) Prior Publication Data
US 2010/0172955 A1 Jul. 8, 2010

Related U.S. Application Data

(63) Continuation of application No. 10/492,580, filed as application No. PCT/GB02/04679 on Oct. 15, 2002, now abandoned.

(30) Foreign Application Priority Data

Oct. 16, 2001 (GB) .................................. 0124742.8

(51) Int. Cl.
*A61K 33/42* (2006.01)
*A61K 33/10* (2006.01)
*A61K 33/14* (2006.01)
*A61K 9/14* (2006.01)
*B29C 45/00* (2006.01)
*A61F 2/00* (2006.01)

(52) U.S. Cl.
USPC ........... 424/423; 264/122; 424/602; 424/687; 424/680; 424/400

(58) Field of Classification Search
None
See application file for complete search history.

(56) References Cited

U.S. PATENT DOCUMENTS

| 4,612,923 A * | 9/1986 | Kronenthal ..................... 606/77 |
| 4,942,875 A * | 7/1990 | Hlavacek et al. ............. 606/230 |
| 5,084,050 A | 1/1992 | Draenert |
| 5,679,723 A | 10/1997 | Cooper et al. |
| 5,766,618 A | 6/1998 | Laurencin et al. |
| 6,054,400 A * | 4/2000 | Brink et al. ..................... 501/63 |

FOREIGN PATENT DOCUMENTS

| CN | 1267554 | 9/2000 |
| EP | 0 795 336 | 9/1997 |
| EP | 1 121 943 | 8/2001 |
| JP | 10-52485 A | 2/1998 |
| JP | 10179715 A | 7/1998 |
| JP | 2000-157626 A | 6/2000 |
| WO | WO97/10010 | 3/1997 |
| WO | WO 00/13717 | 3/2000 |
| WO | WO00/21470 | 4/2000 |
| WO | WO03/033042 | 4/2003 |

OTHER PUBLICATIONS

N.L. Ignjatovic, et al., "Microstructural Characteristics of Calcium Hydroxyapatite/poly-L-lactide Based Composites", Journal of Microscopy, Nov. 1999, pp. 243-248, vol. 196, Pt. 2.
Nenad Ignjatovic, et al., "Synthesis and Properties of Hydroxyapatite/poly-L-lactide Composite Biomaterials", Biomaterials, 1999, pp. 809-816, vol. 20, No. 9.
Y. Shikinami, et al., "Bioresorable Devices Made of Forged Composites of Hydroxyapatite (HA) Particles and Poly-L-lactide (PLLA): Part I. Basic Characteristics", Biomaterials, 1999, pp. 859-877, vol. 20, No. 9.
Yoshihito Ohnaka, "Biodegradable Composite Material by Hydroxyapatite and Poly L-lactic Acid", Aichi Medical University, 1998, pp. 225-239, vol. 26, No. 4/5.
Machine Translation of JP 2000-157626 A 15 pages, Jun. 13, 2000.
Machine Translation of JP 10-52485 A 18 pages, Feb. 24, 1998.
WO03/033042 Biocomposites Ltd. with International Search Report, Apr. 24, 2000.
WO00/21470 Therics, Inc. et al. with International Search Report, Apr. 20, 2000.

* cited by examiner

*Primary Examiner* — Patricia A Duffy
*Assistant Examiner* — Garen Gotfredson
(74) *Attorney, Agent, or Firm* — Tarolli, Sundheim, Covell & Tummino LLP

(57) ABSTRACT

A biodegradable material for use in making items usable in surgery and related fields of medicine. The material comprising a bioabsorbable thermoplastic polymer component and a bioactive filler material. In components made of the material particles of the filler material occur embedded within the surface of the components.

17 Claims, 1 Drawing Sheet

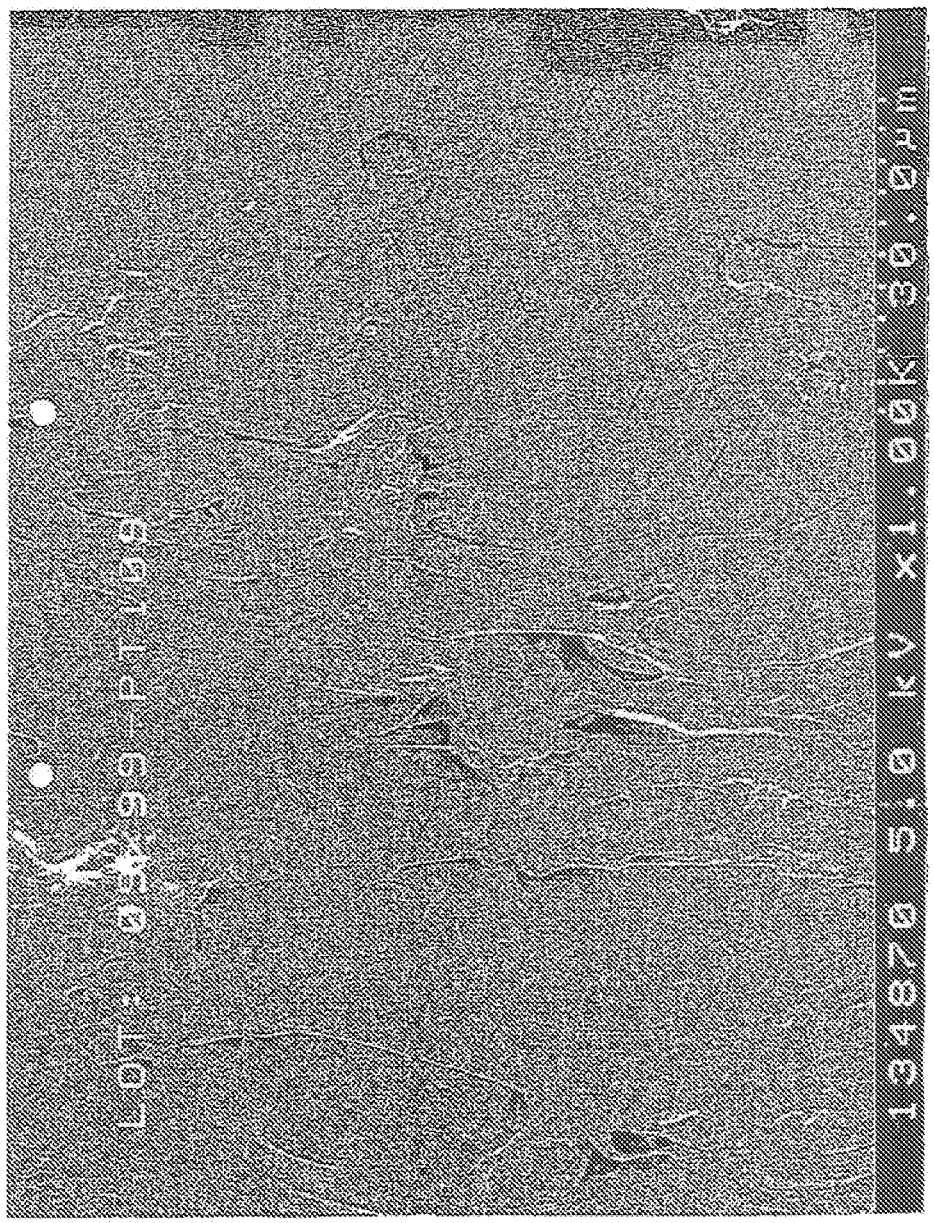

BIODEGRADABLE MATERIAL COMPONENTS

CROSS REFERENCES TO RELATED APPLICATIONS

The following application is a continuation application that claims priority to U.S. application Ser. No. 10/492,580 filed under 35 U.S.C §371 on Apr. 14, 2004 (Now Abandoned) that claims priority to International Application Serial Number PCT/GB02/04679 filed Oct. 15, 2002 which claims priority to Great Britain Application Serial Number 0124742.8 filed Oct. 16, 2001. This application incorporates the above-identified applications herein by reference in their entirety and claims priority all forementioned applications for all purposes.

FIELD OF THE INVENTION

This invention concerns components made of biodegradable materials, a method of making such materials, such materials, and a method of making such components.

Orthopaedic surgery, craniofacial surgery and related fields of medicine require the use of materials which are suitable as implants and prostheses, for example to fill voids created by surgical removal of bone or tissue, or in the formation of screws, pins or plates to hold together bone surfaces or attach ligaments or tendons whilst natural healing takes place. Such materials must, particularly when they are used as load bearing implants, possess good mechanical strength and a sufficiently high Young's modulus to provide secure fixation. Commonly used prosthetic materials include metals such as cobalt—chromium alloys, titanium and stainless steel. Many studies however, have shown that the high rigidity of these materials can prevent complete healing since much of the load which is normally carried by the bone is transferred across the defect site by the implant i.e. producing a stress shielding effect. In addition, metallic implants can have a number of other disadvantages including long term metal ion release and often the need for further surgery to remove the implant.

Bioabsorbable polymers are a class of materials that are now being used in a wide range of medical applications. These include soft tissue support such as sutures and wound care patches and hard tissue repair and fixation such as plates, screws and pins. The rate of healing of bone and the establishment of viable haversian systems is about six weeks in man and hence materials for fracture support should maintain adequate strength and modulus throughout this time frame.

BRIEF SUMMARY OF THE INVENTION

The invention provides a component made of a biodegradable material which material comprises a bioabsorbable polymer component and a bioactive filler material, wherein particles of the filler occur embedded within the surface of the component.

The component may comprise any of a screw, pin, plate, suture, wound care patch, spinal spacer, osteotomy wedge, cement restrictor, non-woven mesh or other item usable in surgery and related fields of medicine.

According to the present invention there is also provided a method of making a biodegradable material, the method comprising mixing together a bioabsorbable polymer component and a bioactive filler material.

The polymer component and filler are preferably mixed together in the form of granules each having similar particle size ranges. The particle size may be between 0.5 mm and 5 mm.

The polymer component and filler may be mixed together in the form of dry particulate materials.

Alternatively the polymer component may be coated with the filler.

The polymer component may be wetted with a solvent prior to or during mixing and the solvent may comprise chloroform. The polymer component may be sprayed onto the filler.

The material is preferably subsequently dried to remove the solvent.

The particle size of the polymer component may be reduced prior to mixing with the filler. The polymer component may be milled and may be cryogenically mined.

The particle size of the filler may be increased prior to mixing with the polymer component, and the filler material may be caused to agglomerate or granulate.

The invention further provides a biodegradable material, the material being formed by a method according to any of the preceding eight paragraphs.

The mixture is preferably substantially homogeneous.

The polymer component is preferably synthetic, and may comprise a polyester.

The polymer component preferably comprises one or more polymers or co-polymers of lactic add (L and/or D), glycolic add, hydroxybutyric add, hydroxyvaleric acid, poly dioxanone, poly caprolactone, poly ethylene oxide or poly butylene terephthalate.

The filler may comprise alone or in combination, a calcium phosphate, calcium sulphate or carbonate bioceramic filler, or a bioactive glass. The filler preferably comprises hydroxyapatite and/or beta tri-calcium phosphate.

The filler preferably has a particle size of substantially less than 100 microns. The filler preferably constitutes between 1% and 50% of the mixture by weight, and desirably between 15% and 35%.

The filler may additionally comprise, alone or in combination, a sacrificial porosifier. The sacrificial porosifier may comprise a water soluble, heat stable inorganic salt. The inorganic salt may comprise sodium chloride. The sodium chloride may be in the form of a finely divided powder. The sodium chloride may constitute between 1% and 50% by weight of the material The material preferably substantially comprises no mechanically free filler particles with a diameter less than 100 microns.

The invention also provides a method of making a component, the method comprising moulding a material according to any of said preceding eight paragraphs.

The moulding may be in the form of injection moulding, compression moulding, extrusion, extrusion followed by drawing, melt spinning or other melt forming technique.

The material is preferably fed to a moulding machine, with at least a substantial proportion of the material in the form of granules with a diameter of between 0.5 and 5 mm.

The material may be dried prior to moulding.

The component may be annealed subsequent to moulding.

BRIEF DESCRIPTION OF THE DRAWING

The accompanying drawing is a SEM micrograph illustrating calcium phosphate filler particles shown in the surface by the letter X.

DETAILED DESCRIPTION OF THE INVENTION

Embodiments of the present invention will now be described by way of example only, and with reference to the single accompanying drawing which is a SEM micrograph of the surface of a component according to the invention.

Example 1

A poly L-lactide (PLLA) of molecular weight 200,000 Daltons and mean granule size of 4 mm was added to a pan granulator together with a poly crystalline micro porous beta tri-calcium phosphate (TCP) powder of mean particle size 10 microns and having no particles greater than 50 microns diameter. The crystallite size of the beta TCP was approximately 1 micron. The ratio of polymer to calcium phosphate was 5:1 parts by weight. The pan granulator was set in motion and a spray of chloroform was directed at the tumbling mass of granules. The PLLA immediately became wetted by the chloroform and the TCP powder adhered to the resulting "sticky" polymer surface. When all of the TCP appeared to have coated the PLLA granules the granulation process was stopped. The resultant TCP coated PLLA was dried in an oven at 100° C. for 4 hours to remove all traces of chloroform and then fed into an injection moulding machine where bony site implantation devices were moulded. A microscopic examination of the surface of the moulded components revealed calcium phosphate particles embedded within and exposed at the said surface.

Example 2

A poly L-lactide of molecular weight 200,000 Daltons and mean granule size of 4 mm was cryogenically milled to give polymer flakes of size range approximately ½ mm to 1½ mm with an absence of finer material.

A beta tri-calcium phosphate powder of mean particle size 10 microns and having no particles greater than 50 microns diameter was dispersed in water. The resulting slurry was de-watered on a Buchner filter and the resulting filter cake was dried. The dry cake was lightly crushed and sieved to give loose agglomerates in the size range of approximately ½ mm to 1½ mm. These agglomerates were now lightly sintered followed by dry mixing with PLLA flakes in the proportions PLLA:TCP, 3:1 by weight. The resulting mix could now be fed through the hopper into the injection moulder without problems of de-mixing or bridging. Inside the moulding machine the high shear conditions within the viscous polymer melt caused break-up of the lightly sintered TCP agglomerates. Moulded composite implantation devices were produced which had a uniform dispersion of TCP particles of substantially less than 100 micron diameter within both the bulk and the surface of the polymer matrix.

Example 3

A hydroxyapatite (HA) powder having a maximum particle size of about 50 microns was put into a pan granulator. While tumbling, the HA powder was sprayed with a solution of poly L-lactide of molecular weight 150,000 Daltons in chloroform at a concentration of 2 gms PLLA in 100 ml of chloroform. Spraying was stopped when the granules reached a maximum size of approximately 3 mm. The product was dried at 100° C. for 2 hours to remove residual solvent and any remaining powder less than 500 micron particle size was sieved out of the mix. The granulated HA was now dry blended with PLLA granules of molecular weight 220,000 Daltons and particle size 2 mm to 3 mm in a weight ratio of PLLA:HA, 2:1. The mixture was fed to an injection moulding machine and moulded components were produced which had HA particles embedded within their surface and throughout their bulk

Example 4

A poly L-lactide of molecular weight 200,000 Daltons and mean granule size of 4 mm was cryogenically milled to give polymer flakes of size range approximately ½ mm to 1½ mm with an absence of finer material.

A lightly sintered polycrystalline hydroxyapatite powder having a particle size of about 100-250 microns was dry blended with the PLLA flakes in the proportions PLLA:HA 3:1 by weight and the mixture was heated to 145° C. for ½ hour. This temperature is not so high as to melt the polymer and start the degradation process but is sufficient to give some "stickiness" and hence cohesion between the polymer and the HA. The hot mixture was stirred together and fed to an injection moulding machine. Moulded components were produced which had HA particles embedded within their surface.

Example 5

A calcium Carbonate (CC) powder having a maximum particle size of about 50 microns was put into a pan granulator. While tumbling, the CC powder was sprayed with a solution of poly L-lactide of molecular weight 150,000 Daltons in chloroform at a concentration of 2 gms PLLA in 100 ml of chloroform. Spraying was stopped when the granules reached a maximum size of approximately 3 mm. The product was dried at 100° C. for 2 hours to remove residual solvent and any remaining powder less than 500 micron particle size was sieved out of the mix. The granulated CC was now dry blended with PLLA granules of molecular weight 220,000 Daltons and particle size 2 mm to 3 mm in a weight ratio of PLLA:CC, 2:1. The mixture was fed to an injection moulding machine and moulded components were produced which had CC particles embedded within their surface.

Example 6

A material was prepared according to any of the methods described in Examples 1 through 5. However the bioabsorbable polymer component was a poly L-lactide having a molecular weight of 450,000 Daltons.

Example 7

A material was prepared according to any of the methods described in the preceding examples. In each case the filler component included a proportion of sodium chloride ranging between 1% and 99% of the total weight of the filler.

SEM micrographs of the surfaces of components produced by the above methods show filler particles embedded within the surface of the components, and uniformly distributed therein. The accompanying drawing shows such a micrograph with calcium phosphate filler particles shown in the surface by the letter X.

There is thus described a biologically acceptable material and injection or compression moulded components made from this material, along with a method of making the material and the components. The components can be used as prosthesis devices which have mechanical properties much closer to natural bone than those for instance of metals or polymers. The materials are at least partially bioabsorbable as a result of the nature of the materials. Such components do not therefore require to be removed from the body following natural healing.

Polyester polymers degrade through hydrolysis of the ester bond in the polymer backbone to produce simple acid repeat units which can be safely metabolised by the body. The degradation rate depends upon the hydrophilic/hydrophobic nature of the polymer along with the molecular weight (Mw), and degree of crystallinity. The rate of degradation is chosen to allow the healing bone to gradually restore its physiological load-bearing function.

It is to be realised that materials having differing rates of resorption can be obtained by selection of different polymers or combinations of polymers, or different Mw, or proportions of filler material. The presence of filler particles moulded within the surface of the components provides a surface which is less hydrophobic and more amenable to early cellular attachment and proliferation than a simple polymer surface. The inclusion of particles of a sacrificial porosifier enables the production of component implant devices that contain less polymer and that have a controlled porosity pre or post implantation.

The powder feed to the moulding machine contains no mechanically free filler particles substantially less than 100 microns diameter, as the particles are either loosely bound together, and/or are loosely bound with the polymer. The moulded component though contains no filler particles substantially greater than 100 microns diameter. Coarser particles in the moulded component could result in flaws or centres of weakness.

The addition of fillers can provide a number of advantages such as resulting in increasing modulus such that matching of the modulus to bone can be achieved or at least approached. Hydroxyapatite or beta tri-calcium phosphate are osteoconductive which helps to provide an environment for new bone in-growth as the polymer resorbs. These filler materials have a radio density similar to bone and therefore help to enable the implant to be imaged using standard X-ray techniques. The fillers can also help to prevent the lowering of pH which can occur during degradation of the polymers due to the add products being released, which may not be able to diffuse sufficiently quickly away. The powder feed to the moulding machine contains filler particles which are not fully encapsulated by the polymer and have not been compounded by a melting process. Such melting would tend to prevent filler particles being provided on the surface of the components.

Various other modifications may be made without departing from the scope of the invention. For instance, different materials may be usable. Instead of the fillers indicated in the examples, other bioactive materials could be used such as calcium carbonate, calcium sulphate or bioactive glass. The filler may comprise a sacrificial porosifier other than sodium chloride which may additionally comprise and constitute a therapeutic agent for controlled release. The conditions during formation of the material and the components can be adjusted as is required. The components may be annealed to remove stresses following formation. Moulding techniques other than injection moulding may be used, such as compression moulding, melt spinning or extrusion. The components may be drawn in order to align the polymer chains following formation. Alternative solvents to chloroform may be used.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method of making a component, the method comprising mixing together, without melting, a bioabsorbable polymer material and a bioactive filler material in the form of dry particulate materials, wherein an amount of heat is applied during the mixing, the amount of heat being below the melting point of the bioabsorbable polymer, but sufficient for the surface of the bioabsorbable polymer to become sticky and aid cohesion; feeding the mixture dry to an injection moulding machine and injection moulding the mixture to form the component such that particles of the filler occur embedded within and exposed at the surface of the component, such that the particles extend beyond the surface of the component, the particle size of the polymer material being between 0.5 mm and 5 mm, the filler having a particle size of less than 100 μm and constituting between 1% and 50% of the mixture by weight.

2. A method according to claim 1 characterised in that, the mixture fed to the injection moulding machine is homogenous.

3. A method according to claim 1 characterised in that, the polymer material is synthetic.

4. A method according to claim 1 characterised in that, the polymer is a bioabsorbable polymer material.

5. A method according to claim 4 characterised in that, the bioabsorbable polymer material comprises one or more polymers or co-polymers of lactic acid (L and/or D), glycolic acid, hydroxybutyric acid, hydroxyvaleric acid, poly dioxanone, poly caprolactone, poly ethylene oxide or poly butylene terephthalate.

6. A method according to claim 1 characterised in that the filler is a bioactive filler material.

7. A method according to claim 6 characterised in that, the bioactive filler material comprises alone or in combination, calcium phosphate, calcium sulphate or carbonate bioceramic filler.

8. A method according to claim 7 characterised in that, the bioactive filler material comprises hydroxyapatite and/or beta tri-calcium phosphate.

9. A method according to claim 6 characterised in that, the bioactive filler material constitutes between 15% and 35% of the mixture by weight.

10. A method according to claim 1 characterised in that, the polymer material and the filler material are mixed together in the form of granules each having similar particle size ranges.

11. A method according to claim 10 characterised in that, the particle size of the polymer material is reduced prior to mixing with the filler material.

12. A method according to claim 10 characterised in that the particle size of the filler material is increased prior to mixing with the polymer material.

13. A method according to claim 4 characterised in that; the bioabsorbable polymer material comprises a polyester.

14. A method according to claim 4 characterised in that the bioabsorbable polymer material is in the form of granules.

15. A method of making a component, the method comprising mixing together, without melting, a bioabsorbable polymer material in the form of granules and a bioactive filler material in the form of dry particulate materials, wherein an amount of heat is applied during the mixing, the amount of heat being below the melting point of the bioabsorbable polymer, but sufficient for the surface of the bioabsorbable polymer to become sticky and aid cohesion, feeding the mixture dry to an injection moulding machine and injection moulding the mixture to form the component such that particles of the filler occur embedded within and exposed at the surface of the component such that the particles extend beyond the surface of the component, the particle size of the polymer material being between 0.5 mm and 5 mm, the filler having a particle size of less than 100 µm and constituting between 1% and 50% of the mixture by weight, the polymer material comprising one or more polymers or co-polymers of lactic acid (L and/or D), glycolic acid, hydroxybutyric acid, hydroxyvaleric acid, poly dioxanone, poly caprolactone, poly ethylene oxide or poly butylene terephthalate.

16. A component made according to the method of claim 15 characterised in that the component comprises items such as screws, pins, plates, sutures, spinal spacers, osteotomy wedges, cement restrictors or other items usable in surgery and related fields of medicine.

17. A method according to claim 6 characterised in that the bioactive filler material is in the form of granules.

\* \* \* \* \*